(12) United States Patent
Geistlich et al.

(10) Patent No.: US 7,141,072 B2
(45) Date of Patent: Nov. 28, 2006

(54) METHOD FOR PROMOTING REGENERATION OF SURFACE CARTILAGE IN A DAMAGED JOINT USING MULTI-LAYER COVERING

(75) Inventors: Peter Geistlich, Stansstad (CH); Lothar Schloesser, Darmstadt (DE)

(73) Assignee: Ed. Geistlich Soehne AG fuer Chemische Industrie, Wolhusen (CH)

( * ) Notice: Subject to any disclaimer, the term of this patent is extended or adjusted under 35 U.S.C. 154(b) by 10 days.

(21) Appl. No.: 09/925,728

(22) Filed: Aug. 10, 2001

(65) Prior Publication Data

US 2002/0013627 A1    Jan. 31, 2002

Related U.S. Application Data

(63) Continuation-in-part of application No. 09/545,465, filed as application No. PCT/GB98/02976 on Oct. 5, 1998, now Pat. No. 6,752,834.

(60) Provisional application No. 60/224,010, filed on Aug. 10, 2000.

(51) Int. Cl.
*A61F 2/28* (2006.01)

(52) U.S. Cl. .................. 623/23.74; 623/23.63; 623/908

(58) Field of Classification Search ............ 623/11.11, 623/18.11, 20.14, 23.74, 23.76, 908, 925, 623/13.11, 14.12, 16.11; 128/898
See application file for complete search history.

(56) References Cited

U.S. PATENT DOCUMENTS

| | | |
|---|---|---|
| 5,167,961 A | 12/1992 | Lussi et al. |
| 5,417,975 A | 5/1995 | Lussi et al. |
| 5,567,806 A | 10/1996 | Abdul-Malak |
| 5,573,771 A | 11/1996 | Geistlich et al. |
| 5,624,463 A | 4/1997 | Stone et al. |
| 5,759,190 A | 6/1998 | Vibe-Hansen |
| 5,837,278 A | 11/1998 | Geistlich et al. |
| 6,221,109 B1 | 4/2001 | Geistlich et al. |

FOREIGN PATENT DOCUMENTS

| | | |
|---|---|---|
| WO | WO 9518638 A1 | 7/1995 |
| WO | WO 9624310 A1 | 8/1996 |
| WO | WO 9625961 A1 | 8/1996 |

OTHER PUBLICATIONS

H.A. Breinan et al., "Reparative Tissues in Articular Cartilage Defects in a Canne Model Treated by Microfracture", 45th Annual Meeting, Orthopaedic Research Society, Feb. 1-4, 1999, Anaheim, CA.

C.R. Lee et al., "Harvest and Selected Cartilage Repair Procedures Affect Mechanical and Biochemical Properties of Uninvolved Articular Cartilage in the Canine Knee", 45th Annual Meeting, Orthopaedic Research Society, Feb. 1-4, 1999, Anaheim, CA.

(Continued)

*Primary Examiner*—Brian E. Pellegrino
(74) *Attorney, Agent, or Firm*—Rothwell, Figg, Ernst & Manbeck, PC

(57) ABSTRACT

A method of promoting regeneration of surface cartilage of a joint includes the steps of covering the area to be treated with a patch which includes a sheet of collagen membrane material. The collagen membrane material has at least one barrier layer to prevent passage of cells therethrough. The collagen membrane further includes a matrix layer predominantly of collagen II having an open sponge-like texture. The patch is fixed over the area to be treated, and the area is allowed to regenerate cartilage.

20 Claims, 4 Drawing Sheets

OTHER PUBLICATIONS

C.R. Lee et al., "The Contractile Behavior of Articular Chondrocytes in Collagen Matrices *In Vitro*", Tissue Engineering Soc., Orlando, Fla., Dec. 4-6, 1998.

S.M. Mueller et al., "Alpha-Smooth Muscle Actin in Bovine Meniscus Cells Seeded in Type I and Type II Collagen-Gag Matrices", 44TH Annual Meeting, Orthopaedic Research Society, Mar. 16-19, 1998, New Orleans, Louisiana.

S. Nehrer et al., "Chondrocyte-Seeded Type I and Type II Collagen Implants Investigated *In Vitro*", Fifth World Biomaterials Congress, May 29-Jun. 2, 1996, Toronto, CA.

S. Nehrer et al., "Autologous Chondrocyte-Seeded Type I and Type II Collagen Matrices Implanted in a Chrondral Defect in a Canine Model", 44TH Annual Meeting, Orthopaedic Research Society, Mar. 16-19, 1998, New Orleans, Louisiana.

S. Nehrer et al., "Chondrocyte-Seeded Type I and Type II Collagen Matrices Implanted in a Chondral Defect in a Canine Model", 7th Conference European Orthopaedic Research Society, Barcelona, 1997.

S. Nehrer et al., "Characteristics of Articular Chondrocytes Seeded in Collagen Matrices *In Vitro*", Tissue Engineering, vol. 4, No. 2, 1998, pp. 175-183.

S. Nehrer et al., "Matrix Collagen Type and Pore Size Influence Behaviour of Seeded Canine Chondrocytes", Biomaterials 18, (1997), pp. 769-776.

Donna Schulz-Torres et al., "Tendon Cell Contraction of Collagen-Gag Matrices *In Vitro*: Effect of Cross-Linking", Soc. for Biomaterials, Providence, R.I., Apr. 28-May 2, 1999.

T.O. Schneider et al., "Expression of $\alpha$-Smooth Muscle Actin in Canine Intervertebral Disc Cells *In Situ* and in Collagen-Gag Matrices *In Vitro*", J. Orthopaedic Research In press, pp. 1-22.

S. Nehrer et al., "Canine Chondrocytes Seeded in Type I and Type II Collagen Implants Investigated *In Vitro*", Jan. 29, 1997, John Wiley & Sons, Inc., pp. 95-104.

S.M. Mueller et al., "$\alpha$-Smooth Muscle Actin and Contractile Behavior of Bovine Meniscus Cells Seeded in Type I and Type II Collagen-Gag Matrices", Sep. 18, 1998, John Wiley & Sons, Inc., 1999, pp. 1-10.

Genzyme Tissue Repair, "CARTICEL™ (autologous cultured chondrocytes), Engineering a Better Repair", Genzyme Tissue Repair, 64 Sidney Street, Cambridge, MA 02139-4136, Sep. 1997, brochure.

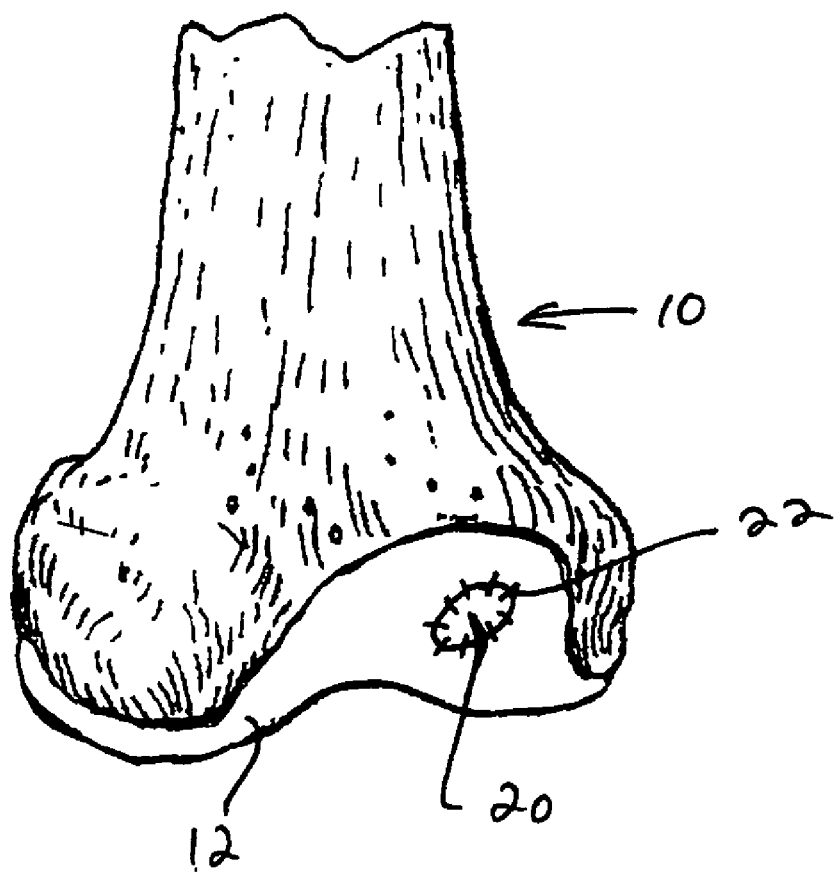

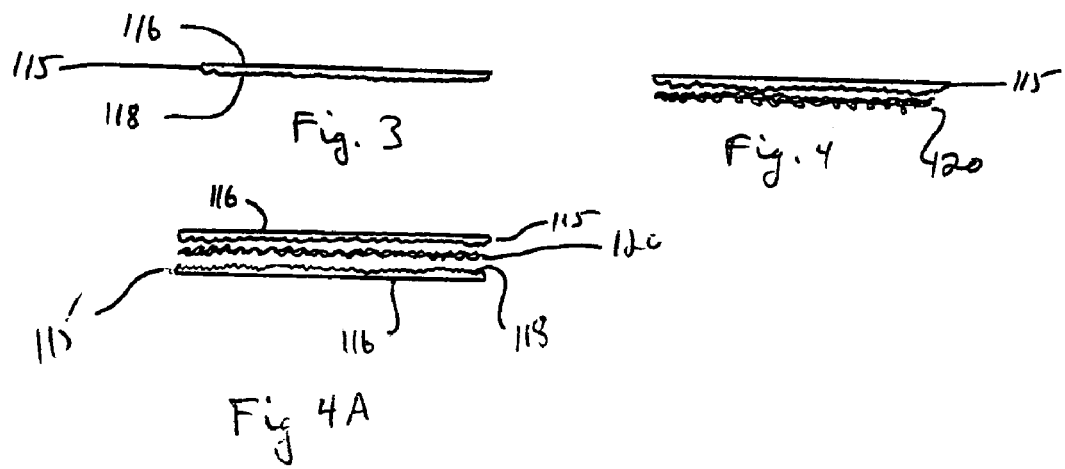

MEHTOD FOR PROMOTING
REGENERATION OF SURFACE CARTILAGE
IN A DAMAGED JOINT USING
MULTI-LAYER COVERING

This application claims the benefit of provisional application Ser. No. 60/224,010, filed Aug. 10, 2000. This application also is a continuation-in-part of U.S. Ser. No. 09/545,465, filed Apr. 7, 2000 now U.S. Pat. No. 6,752,834, which is a §371 of PCT/GB98/02976, filed Oct. 5, 1998.

BACKGROUND OF THE INVENTION

1. Field of the Invention

The present invention relates to the field of promoting regeneration of surface cartilage in damaged joints.

2. Description of the Background Art

In view of the large number of joint injuries, such as knee injuries, which take place yearly, a number of therapies have been developed in an effort to promote regeneration of damaged cartilage. Typical methods involve introduction of chondrocytes from an outside source into the damaged area to promote cartilage regeneration.

For example, in accordance with one method, a cartilage biopsy is surgically removed from the patient and sent to a laboratory, where the patient's chondrocytes are isolated from the cartilage and the chondrocyte cells are reproduced in culture. Later, another surgery is performed on the patient wherein the damaged cartilage area to be treated is debrided back to expose healthy cartilage, leaving the subchondral bone plate intact. A periosteal patch is taken from the proximal medial tibia of the patient, and this periosteal patch is sutured to the rim of the healthy cartilage surrounding the area to be treated. The cultured chondrocytes reproduced from the cells previously taken from that patient then are injected under the patch into the defect, and the injury is allowed to heal.

U.S. Pat. No. 5,759,190 discloses another method, wherein a hemostatic barrier is placed proximal to the surface to be treated, chondrocytes in a matrix are placed upon the surface to be treated distal to the hemostatic barrier, and then the matrix is covered with a patch.

There remains a need in the art for improved methods of promoting regeneration of surface cartilage in damaged joints.

SUMMARY OF THE INVENTION

In accordance with the present invention, a method of promoting regeneration of surface cartilage of a joint includes the steps of covering the area to be treated with a patch comprised of a sheet of collagen membrane material, wherein said collagen membrane material is comprised of at least one barrier layer which acts as a barrier to inhibit passage of cells therethrough, wherein said collagen membrane further comprises a matrix layer predominantly of collagen II having an open sponge-like texture. The patch is fixed over said area, and said area is allowed to regenerate cartilage.

BRIEF DESCRIPTION OF THE DRAWINGS

FIG. 2 is a perspective view with portions broken away showing the bone joint FIG. 1 following covering the injured area with a patch made of a collagen membrane material in accordance with the present invention.

FIG. 3 is a side elevation schematic view showing a membrane for use in accordance with the present invention.

FIG. 4 is a side elevation schematic view showing a double-layer membrane for use in accordance with the present invention.

FIG. 4A is a side elevation schematic view showing a membrane for use in accordance with the present invention, including a collagen II inner layer matrix surrounded by barrier layers having opposite outer barrier faces.

DETAILED DESCRIPTION OF THE INVENTION

The present invention provides a method for repairing injuries and damage to surface cartilage in joints such as knees. In accordance with one embodiment, cartilage defects are removed from the injured area to be treated, for example, by scraping of calcified cartilage from the injured area.

Figure 1:
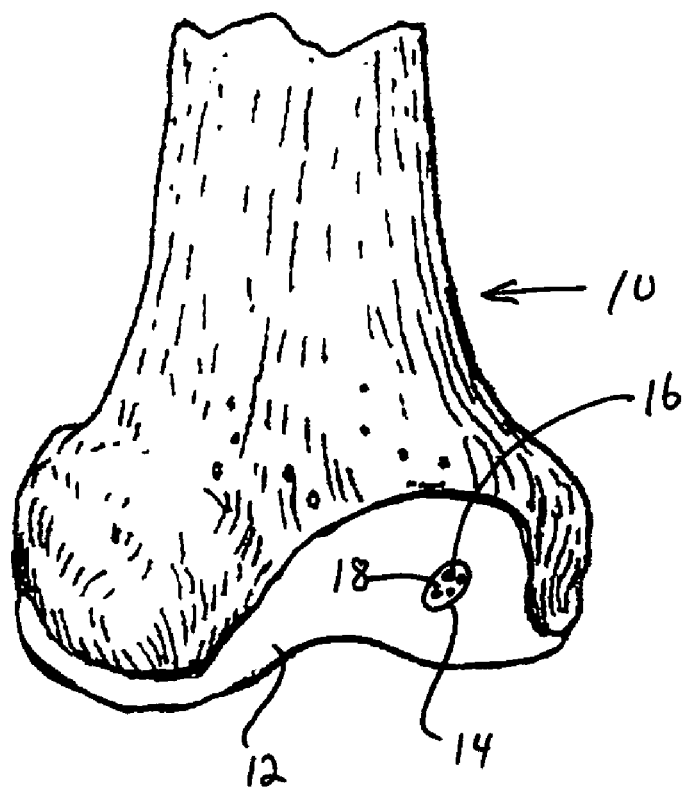
FIG. 1 is a perspective view with portions broken away showing an injured area of surface cartilage of a bone joint end member.

After scraping of the calcified cartilage, a plurality of punctures may be formed in the subchondral plate of the area of injury utilizing a microfracture technique. FIG. 1 shows a bone 10 with cartilage 12 showing an area of injury 14 to be treated, wherein calcified cartilage has been scraped from the area to be treated. A plurality of punctures 16 have been formed in the subchondral plate 18 of the area of injury.

The punctures 16 in the subchondral plate can be formed, for example, with a straight pointed end of a microsurgical pick to a depth of, e.g., about 0.5–5 mm, more preferably about 1.5–2 mm. The punctures 16 may have a width of, for example, about 0.2–1.5 mm, more preferably about 0.5–1 mm, and most preferably about 0.8 mm.

Although the invention has been described with respect to utilization of the above-described microfracture technique involving forming a plurality of punctures in the subchondral plate, it is believed that the invention also is applicable to other methods of puncturing the subchondral plate, such as drilling, abrasion and the like.

After forming the punctures in the subchondral plate as described above, the punctures in the area to be treated can be covered by a patch 20 comprised of a multi-layer of collagen membrane material. The patch can be charged with extracellular cultivated chondrocytes, if desired.

The patch then is fixed over the area to be treated, for example, by sutures 22 as shown in FIG. 2, to fix the patch to or over the healthy cartilage surrounding the area to be treated. Alternatively, the patch may be fixed over the area to be treated by adhesively bonding the patch to or over surrounding healthy cartilage, for example, utilizing an organic glue known in the art, or any other suitable method. The surgical procedure can be open surgery or arthroscopic surgery.

The patched area then is allowed to regenerate cartilage.

The present invention avoids the necessity of providing a separate hemostatic barrier as in U.S. Pat. No. 5,759,190, a separate chondrocyte-charged matrix placed distal to the hemostatic barrier as described therein, and a separate patch covering the matrix as in said patent.

Figure 6:
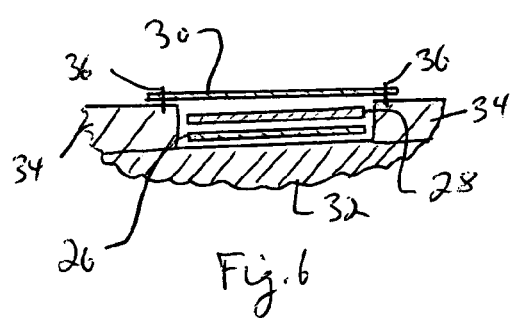
FIG. 6 is a schematic side elevation view, in cross-section, with portions broken away, showing a prior art configuration for addressing surface cartilage injuries in a joint.

FIG. 6 shows a prior-art configuration utilizing a separate hemostatic barrier 26, a separate chondrocyte-charged matrix 28 placed distal to hemostatic barrier 26 and a separate patch 30 covering matrix 28. Hemostatic barrier 26 is placed adjacent bone 32, and patch 30 can be affixed to surrounding cartilage 34 by any suitable means, such as sutures 36.

Figure 7:
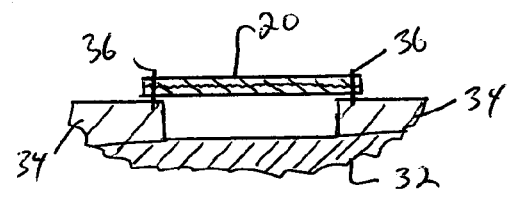
FIG. 7 is a schematic side elevation view in cross-section, with portions broken away, showing utilization of a single, multi-layer patch in accordance with one embodiment of the present invention.

In contrast, in accordance with one embodiment of the invention, a single, multi-layer patch 20 may be affixed to surrounding cartilage 34, as shown in FIG. 7, utilizing any suitable means such as sutures 36. As shown in FIG. 7, no separate hemostatic barrier, apart from patch 20, is applied against bone 32 in the damaged area, when utilizing this embodiment of the present invention.

In accordance with one embodiment, the collagen membrane material is comprised of at least one barrier layer having at least one smooth face 116 so as to inhibit cell adhesion thereon and act as a barrier to prevent passage of cells therethrough. See FIG. 3. In accordance with this embodiment, the barrier layer further has a fibrous face 118 opposite the smooth face 116, the fibrous face allowing cell growth thereon. The smooth face 116 preferably is oriented away from the area to be treated, and the fibrous face 118 preferably is oriented toward the area to be treated. In preferred embodiments, the barrier layer is predominantly collagen I, collagen III or a mixture thereof. One suitable material is Biogide®, from Ed. Geistlich Söhne AG für Chemische Industrie, the assignee of the present invention. The Biogide® material is described in U.S. Pat. No. 5,837,278, incorporated herein by reference.

FIG. 4 shows a multi-layer membrane which may be used in accordance with the present invention. This membrane includes a barrier layer 115 as shown in FIG. 3, and further includes a matrix layer 120 predominantly of collagen II having an open sponge-like texture. A collagen membrane as shown in FIG. 4 is described in PCT Application No. PCT/GB98/02976, U.S. Ser. No. 09/545,465, filed Apr. 7, 2000, claiming priority from U.K. patent application no. 9721585.9, filed Oct. 10, 1997, incorporated herein by reference.

FIG. 4A shows another multi-layer membrane which may be used in accordance with the present invention. This membrane includes a pair of barrier layers 115 sandwiched around a central matrix layer 120 predominately of collagen II having an open sponge-like texture. In accordance with this embodiment, smooth faces 116 of the barrier layers are oriented outwardly, and fibrous faces 118 of barrier layers 115 are oriented inwardly toward matrix layer 120.

U.S. Ser. No. 08/894,517, filed Nov. 10, 1997 (corresponding to WO-A-96/25961), incorporated herein by reference, discloses a matrix implant based on collagen II which can be implanted at the in vivo site and which may utilize growth of native chondrocytes on the surface of the matrix to effect cartilage regeneration.

The present invention also may utilize a matrix implant which will permit successful ingrowth of native chondrocytes and thus regeneration of cartilage tissue following implantation in vivo. Cartilage and ultimately new bone tissue can be reconstructed by the use of a collagen II matrix which in vivo is shielded not only from the surrounding connective tissue but also from the underlying bone or cartilage defect. This may be achieved through the use of a multi-layer membrane implant which itself is capable of preventing the undesired ingrowth of any surrounding tissues into the matrix, or which may be surgically implanted at the site of the defect so as to achieve this effect.

Viewed from one aspect the invention thus provides a multi-layer membrane comprising a matrix layer predominantly of collagen II and having an open sponge-like texture, and at least one barrier layer having a close, relatively impermeable texture.

A particular advantage of the membrane according to the invention when used is that native cells are unable to penetrate or grow into the layer having a close, relatively impermeable texture.

While not wishing to be bound by theory, it is now believed that successful cartilage regeneration requires that the rapid ingrowth not only of native tissue cells, such as connective tissues, blood vessels etc., but also of any new bone tissue into the site of the defect be prevented. This may be achieved using a double-layer membrane in accordance with the invention which serves to shield the collagen matrix from the ingrowth of native tissue cells from one side. During surgical implantation this may be used in combination with a tissue graft, e.g. a periosteal graft, effective to prevent the ingrowth of native tissue cells from the opposing side. Thus, for example, a periosteal graft may initially be sutured in place such that this provides a covering over the bone or cartilage defect. A double-layer membrane of the invention may then be implanted at the site of the defect such that this lies in contact with the graft and may be arranged in such a way that the matrix layer faces toward the bone defect. Alternatively, a double-layer membrane of the invention is initially implanted at the site of the defect with the barrier layer facing toward the bone or cartilage defect. A periosteal graft may then be arranged such that this lies in contact with the matrix layer.

The graft may be adhered with a biocompatible adhesive such as fibrin glue, or pinned with resorbable polylactic pins, or if necessary or possible sutured in such a way that this then serves to provide an impermeable barrier to the ingrowth of any surrounding connective tissue.

In an alternative embodiment of the invention, the membrane itself may be effective to prevent the ingrowth of any native tissue cells. The invention may utilize a membrane comprising at least three layers in which a matrix layer being predominantly made from collagen II and having an open sponge-like texture is provided between two barrier layers having a close, relatively impermeable texture.

The matrix layer is capable of acting as a medium for the ingrowth of native chondrocytes thereby effecting regeneration of cartilage tissue. However, to further aid in regenerating cartilage tissue the matrix layer may be impregnated with chondrocytes either prior to or following implantation in vivo. While the matrix layer may be impregnated with chondrocytes immediately prior to implantation, e.g. by injection, it is expected that in general the chondrocytes will be introduced into the matrix layer by direct injection of a suspension of chondrocytes following implantation. In this way, chondrocytes present in the matrix layer of the membrane are able to effect regeneration of cartilage, and ultimately new bone, while the membrane at the same time prevents the ingrowth of other cell types from the surrounding tissues.

Chondrocytes for use in the invention may be obtained from cell sources which include allogenic or autogenic cells isolated-from articular cartilage, periosteum and perichondrium, and mesenchymal (stromal) stem cells from bone marrow. Since allogenic cells carry the potential for immune response and infectious complications, it is preferable to isolate the chondrocytes from autogenic cells, especially from autogenic articular cartilage. Techniques for harvesting cells are known and include enzymatic digestion or outgrowth culture. The harvested cells are then expanded in cell culture prior to reintroduction to the body. In general, at least $10^6$, preferably at least $10_7$ cells should be impregnated into the matrix layer to provide for optimal regeneration of cartilage tissue.

In general, it is desirable for the matrix layer of the membrane according to the invention to contain glycosaminoglycans (GAGs) such as hyaluronic acid, chondroitin 6-sulphate, keratin sulphate, dermatan sulphate etc. which serve to provide a natural medium in which chondrocytes can become embedded and grow. While it is possible to incorporate into the collagen matrix glycosaminoglycans from different sources which do not necessarily have the same composition, molecular weight and physiological properties as those from cartilage, preferred glycosaminoglycans are those extracted from cartilage itself. In general, the matrix layer preferably contains about 1 to 10 wt % of glycosaminoglycans, for example about 2 to 6 wt %. Although some glycosaminoglycans may be present in the impermeable layer, the greater part will be present in the matrix layer.

In native collagen tissues GAGs occur, at least in part, as a component of proteoglycans (PGs). The use of GAGs in the form of PGs is undesirable in view of potential immunological problems which can be caused by the protein content of the PGs. Preferably, the matrix layer is thus substantially free from any proteoglycans. Conveniently, this may be achieved by preparing the matrix layer from a mixture of a purified telopeptide-free collagen II material and glycosaminoglycans.

Other additives which may also be present in the matrix layer include, for example, chondronectin, laminin, fibronectin, calcium alginate or anchorin II to assist attachment of the chondrocytes to the collagen II fibers, bone and cartilage cell growth-promoting hormones, and growth factors such as cartilage inducing factor (CIP), insulin-like growth factor (IGF), transforming growth factor $\beta$ (TGF$\beta$) present as homodimers or heterodimers, osteogenic protein-1 (OP-1) and bone morphogenetic factors (BMPs) such as native or recombinant human BMP-2, BMP-3 (osteogenin), BMP-4, BMP-7 and BMP-8, or other skeletal matrix molecules, as well as signaling peptides such as transforming growth factor-$\beta$ (TGF-$\beta$, TGF-$\beta$1), vascular endothelial growth factor (VEGF), insulin-like growth factor (IGF), parathyroid hormone related protein (PTHrP) and platelet derived growth factor (PDGF).

The product used in the invention also may act as a carrier for stem cells committed to a particular line of differentiation such as articular cartilage or bone. Such stem cells may be grown in vitro to increase their numbers, and applied to the repair sites in the carrier matrices with or without growth factors. Examples include mesenchymal stem cells and bone marrow stromal cells.

BMP-2 affects the two pathways of bone formation independently—the direct formation of bone as well as the formation of cartilage which is then removed and replaced by bone. Composites of BMPs and collagen including bone matrix obtained by extraction from cortical bone from various sources or demineralized bone matrix comprise about 90% collagen and about 10% non-collagenous proteins (NCP) for BMP activity or for BMP/NCP induced chondrogenesis. Bone matrix-insoluble collagenous matrix and laminin or fibronectin act as carriers for BMPs. Some growth factors may also be present in the impermeable layer. However, preferably the greater part will be present in the matrix layer. In general, the membrane contains from about 100 µg to about 5 mg of growth factors.

A matrix material for use in accordance with the present invention may also be charged with parathyroid hormone (PTH), a polypeptide involved in regulation of calcium in the body.

As indicated above, the membrane comprises at least two layers having different structures. Preferably, the barrier layer of the membrane is predominantly made from collagen I and III. Alternatively, this may comprise a synthetic material, e.g. a synthetic resorbable polymer network optionally coated with a collagen material such as type I and/or type III collagen.

Examples of suitable synthetic materials include polyesters, polyglycolic and polylactic acids (PLA) homopolymers and copolymers, glycolide and lactide copolymers, polyorthoesters and polycaprolactones. Many examples of these are openly available, e.g. from Boehringer Ingelheim in their RESOMER range. PLA polymers as wax with an appropriate molecular size of ca. 650–1200 and not too rapid a degradation are preferred. A particularly preferred biodegradable polymer is poly(D,L-lactic acid) in which the ratio of D-lactide to L-lactide is approx. 70:30. An advantage of such synthetic materials is that these can have high mechanical stability which allows the membrane implant to be stretched over complex, three dimensional bone defects without tearing. Such materials are also suitable for suturing.

Advantageously, the barrier layer barrier layer structure is primarily made up of long collagen fibers which are so closely connected that high molecular substances cannot permeate this barrier. The long fibers provide high tensile strength and resistance to tearing so that the material is not only a good separation membrane but can also be readily sewn. It is often important in surgery that membrane implants can be sewn or pinned into position and many of the membranes which have previously been proposed do not provide this capability. A preferred membrane for use in accordance with the invention is mechanically stable enough to be handled surgically for implantation.

The matrix layer may be very porous and may have a specific weight as low as 0.02, which permits cells very rapidly to grow into this layer. This layer of the membrane, which may also contain glycosaminoglycans, may swell strongly and can take up as much as 5000% of liquid. Ideally, the matrix layer should provide a pore structure (pore volume fraction and pore size) which allows cell adhesion and growth and which permits the seeded cells to maintain the chondrocytic phenotype, characterized by synthesis of cartilage-specific proteins. Pore sizes will depend on the process (e.g., freeze drying) used to produce the collagen II matrix, but can be expected to be in the range of from about 10 to about 100 µm, e.g. 20 to 100 µm, e.g. about 85 µm. Such a pore size may readily be obtained by slow freezing at about −5 to −10° C. for about 24 hours followed by freeze-drying, or by adding ammonium bicarbonate to the slurry before lyophilization.

The matrix layer of the membrane is preferably provided by collagen II material obtained from cartilage, preferably hyaline cartilage from pigs.

While the desired thickness of the matrix layer will depend upon the nature of the bone or chondral defect to be treated, in general this can be expected to be in the range of from about 0.2 to about 12 mm, e.g. from about 1 to about 6 mm. The thickness of the barrier layer is preferably from about 0.2 to about 2 mm, e.g. from about 0.2 to about 0.7 mm. The final patch thickness may be about 20–120 mm, preferably about 60–100 mm.

The barrier layer may be provided by a natural animal membrane comprising collagen I and III. Being derived from a natural source, this is totally resorbable in the body and does not form toxic degradation products. Such membranes also have particularly high tear strength in either a wet or dry state and can therefore be surgically stitched if necessary. When moist the material is very elastic which allows this to be stretched over irregularly shaped bone defects.

Besides collagen, natural animal membranes contain many other biomaterials, which must be removed. It is known to treat such membranes with enzymes, solvents or other chemicals to effect purification and to use these membranes in medicine. Most of these materials are too thin and very often not particularly easy to use. The collagen fibrils have lost their native character and further disadvantages are that the material often has insufficient strength for use as a sewable material, has no water-swelling properties and provides no difference between the smooth grain side and the fibrous flesh side. The fibrous form of purified telopeptide-free collagen Type I or II, being less soluble and biodegradable, has been found to provide the most advantageous carrier material.

Membranes providing the barrier layer of the product according to the invention include peritoneum membrane from calves or pigs which retain their natural collagen structure. Peritoneum membranes from young pigs aged 6–7 weeks old (weighing 60–80 kg) are especially preferred.

The barrier layer should preferably comprise pure, native (not denatured) insoluble collagen and may be prepared in accordance with the method described in U.S. Pat. No. 6,837,278 (corresponding to WO-A-95/18638). The natural membrane may thus first be treated with alkali, for example aqueous NaOH at a concentration of about 0.2–4% by weight. This serves to saponify any fats and also proteins which are sensitive to alkali. The second step is the treatment of the material with an acid, usually an inorganic acid such as HCl. This eliminates acid-sensitive contaminants. The material is subsequently washed until the pH is in the range about 2.5–3.5. The membrane then has a smooth or grain side and a looser more fibrous side. It may be beneficial to effect some cross-linking of the membrane by heating to 100–120° C.

The collagen II material used to provide the matrix layer of the membrane can be obtained from cartilage by a similar procedure to that described above in relation to the barrier layer comprising predominantly collagen I and III. It is preferable to remove water from the cartilage by treatment with acetone followed by extraction of fat with a hydrocarbon solvent such as n-hexane, though alkanols such as ethanol, ethers such as diethyl ether or chlorinated hydrocarbons such as chloroform, or mixtures thereof may be used. The defatted material is then subjected to treatment with alkali which saponifies any residual fat and degrades some of the proteins present. Finally, the material is treated with acid which effects further protein degradation. The material is allowed to swell in water and is passed through a colloid mill to produce a slurry.

To produce the multi-layer membrane, the soft slurry containing collagen II is applied to the fibrous side of the smooth membrane prepared, for example in accordance with U.S. Pat. No. 5,837,278. Normally, the membrane will be placed on a smooth surface with the grain side down so that the collagen II slurry can readily be applied, e.g. by rubbing into the fibrous side of the membrane. The slurry thus forms a layer of any desired thickness which firmly adheres to the collagen membrane. The double-layer so formed is then subjected to freezing and freeze-drying to provide the desired sponge-like structure having a desired pore size. If necessary, some of the matrix layer may be removed to provide a double-membrane of uniform thickness. To produce a three-layer membrane, a second smooth membrane is then placed on top of the matrix layer with its fibrous side in contact with the matrix layer.

The collagen II slurry to be applied to the membrane in general contains about 1.0–4.0 weight % of the collagen, advantageously about 2–3 weight %. Conveniently, the pH value of this mixture should be adjusted to about 2.5–4.5, advantageously about 3.0–4.0.

The collagen II material further may be cross-linked after the freeze-drying step to stabilize the matrix layer. This also serves to increase the mechanical stability of the matrix layer and to reduce its rate of resorption by the body. Ideally, the degree of cross-linking should be such that the rate of degradation of the matrix matches the rate of tissue regeneration. Physically, cross-linking may be carried out by heating, but this must be effected carefully to avoid undesired loss of resorbability. Heating to temperatures of 100–120° C. for a period of from about 30 minutes to about 5 hours is preferable. More preferably, cross-linking may be effected by UV irradiation using a UV lamp, e.g. for a period of up to 8 hours.

The collagen II material advantageously contains glycosaminoglycans (GAGs). The latter actually reacts with the collagen II to effect some cross-linking and produces an insoluble product. If necessary, further cross-linking can be effected by heating the material or by UV irradiation as discussed above. The reaction between the glycosaminoglycans and the collagen can be effected at ambient temperatures at a pH in the range 2.5–3.5. The quantity of glycosaminoglycan may be between about 1 and about 10% by weight. The material may be subjected to freezing and freeze-drying immediately after such treatment.

For example, GAGs such as chondroitin sulphate (CS) may be covalently attached to the collagen matrix using 1-ethyl-3-(3-dimethyl aminopropyl) carbodiimide (EDC) and N-hydroxysuccinimide (NHS) utilizing known methods. EDC/NHS crosslinking may be utilized for immobilizing GAGs with collagen matrices, which may include dermatan sulphate, heparin and heparan sulphate, as well as CS as indicated above. Such GAGs may be carried by a patch in accordance with the present invention so as to facilitate healing.

Slurry formation may be effected by raising the pH of the collagen II mass. In this procedure, the mass is cooled to about 4° C. and the pH value slowly raised by addition of cold aqueous NaOH at 4° C. up to a pH value about 6.5–7.5. Subsequently, the mass is held at ambient temperature for about 15–25 hours. In this time, the slurry is formed and after slurry formation, the mass can be frozen and freeze-dried.

A still further alternative is to neutralize the collagen II mass to a pH value about 6.8–7.4, subsequent to removal of air. The mixture is placed in the mold and incubated for about 15–20 hours at 37° C. A fine slurry develops which can subsequently be frozen and freeze-dried.

Which of the above methods is used depends upon the properties of the desired product. The first process gives the most stable product. However, the precipitation may give clumps of material and must be very carefully carried out. The second method gives a soft and uniform product which is, however, more soluble than the product of the first process.

In the production of the slurry, it is possible to additionally introduce further desirable substances such as medicines, e.g. antibacterials such as taurolidine and/or taurultam or antibiotics such as gentamycin.

After the application of the slurry to the membrane, the material is frozen. In order to obtain a reproducible pore size, the freezing must be carefully controlled and the rate and time of freezing, the pH value and the particle size must be accurately controlled. In order to obtain very small pores, the material may be shock frozen at very low temperature.

The frozen membrane is then freeze-dried and subsequently heated to about 110–130° C. In this way, some cross-linking is effected. Subsequently, the freeze-dried biomembrane may be adjusted to the required thickness so that the thickness of the matrix layer is commonly about 2 mm. The double membrane is then sterilized, for example by gamma-irradiation or with ethyleneoxide. Sterilization by strong irradiation e.g. with $^{60}$Co in doses of 25 kGy may deactivate the BMPs. In such circumstances, the sterile matrix may be impregnated with BMPs in sterile saline prior to implantation.

The membrane according to the invention can be used in medicine in the following ways:

As a material for guided tissue regeneration, cell growth is encouraged by the matrix layer. The barrier layer inhibits undesired cell growth.

As a material for the repair of chondral defects, i.e. lesions which do not penetrate the subchondral plate, and in the repair of osteochondral defects.

The invention also provides the use of a multi-layer collagen membrane as described above in guided-tissue regeneration. The collagen II content of the membrane is particularly suitable for regeneration of cartilage tissue but is also suitable for other tissue types.

Viewed from a further aspect the invention thus provides a membrane as hereinbefore described for use as a guided tissue regeneration implant.

The invention further provides a method of treating a bone or cartilage defect in the human or non-human animal body, said method comprising application of a membrane as hereinbefore described to the defect, said membrane being oriented such that the barrier layer prevents the ingrowth of undesirable tissue types into the area of bone or cartilage regeneration.

Figure 5:
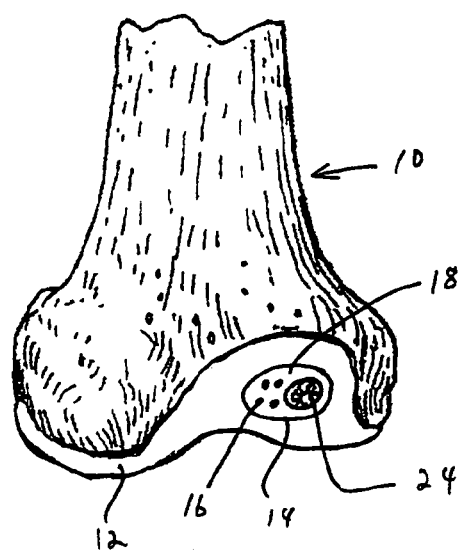
FIG. 5 is a perspective view of the bone joint end member with portions broken away, showing subchondral puncturing and a bone mineral implant in accordance with another embodiment of the present invention.

In accordance with another embodiment, involving more substantial injuries which include injuries to the underlying bone as well as to the surrounding surface cartilage of a joint, an implant material 24 such as resorbable bone mineral may be implanted into the bone injury within the area to be treated. See FIG. 5. The bone mineral may be charged with chondrocytes, if desired. Punctures 16 may be made in the subchondral plate area 18 to be treated, and thereafter, a collagen membrane patch can be fixed over the area to be treated as shown in FIG. 2.

One suitable implant material is Bio-Oss® from Ed. Geistlich Söhne AG Für Chemische Industrie, the assignee of the present invention. Bio-Oss® is described in U.S. Pat. Nos. 5,167,961 and 5,417,975, incorporated herein by reference. Another suitable implant material is Bio-Oss Collagen® from Ed. Geistlich Söhne AG Für Chemische Industrie, which is resorbable bone mineral in a collagen matrix. Bio-Oss Collagen® is described in U.S. Pat. No. 5,573,771, incorporated herein by reference.

The bone mineral may be charged with any of the additives, growth factors and the like which are listed above in connection with charging of the collagen matrix.

Since many modifications, variations and changes in detail may be made to the described embodiments, it is intended that all matter in the foregoing description and shown in the accompanying drawings be interpreted as illustrative and not in a limiting sense.

The invention claimed is:

1. A method of promoting regeneration of surface cartilage of a joint, comprising:

covering an area of damaged cartilage of a joint to be treated with a patch consisting essentially of a multi layer sheet of collagen membrane material, wherein said multi layer sheet of collagen membrane material is comprised of at least one barrier layer which acts as a barrier to inhibit passage of cells therethrough, wherein said at least one barrier layer has a thickness of about 0.2–2 mm and has a structure consisting essentially of collagen I, collagen III or mixtures thereof, wherein said sheet of collagen membrane material further comprises a matrix layer having a thickness of about 0.2–12 mm and having a matrix structure which consists essentially of collagen II having an open sponge like texture; wherein said barrier layer has at least one smooth face so as to inhibit cell adhesion thereon, said barrier layer further having a fibrous face opposite said smooth face, wherein said matrix layer is adhered to said fibrous face;

fixing the patch over said area with the at least one said barrier layer oriented away from the damaged area, and said matrix layer with a matrix structure consisting essentially of collagen II oriented toward the damaged area wherein said patch is fixed over the damaged area without application of a separate hemostatic barrier layer in said area; and allowing said area to regenerate cartilage.

2. The method of claim 1, wherein said barrier layer, said matrix layer or both, are impregnated with glycosaminoglycan.

3. The method of claim 2, wherein the glycosaminoglycan is hyaluronic acid, chondroitin 6 sulphate, keratin sulphate or dermatan sulphate.

4. The method of claim 1 wherein the patch is fixed over the area to be treated by adhesively bonding the patch to cartilage surrounding said area to be treated.

5. The method of claim 1 wherein the patch is fixed over the area to be treated by suturing the patch to cartilage surrounding said area to be treated.

6. The method of claim 1 wherein said membrane material carries at least one pharmaceutically or biologically active substance or mesenchymal stem cells having ability to differentiate into cells to regenerate cartilage or bone.

7. The method of claim 6 in which the pharmaceutically acfive substance is selected from the group consisting Taurolidine, Taurultam and a mixture thereof.

8. The method of claim 6 in which the pharmaceutically active substance is selected from the group consisting of cell growth promoting hormones, bone morphogenetic proteins (BMPs), other skeletal matrix molecules, and signaling peptides.

9. The method of claim 6 wherein the pharmaceutically active substance is selected from the group consisting of BMP-2, BMP-3, BMP-4, BMP-7, BMP-8, OP-1, PTH, TGF-β, TGF-β1, VEGF, CIP, IGF, PTHrP, PDGF and mixtures thereof.

10. The method of claim 1 wherein said membrane material carries articular cartilage stem cells or bone stem cells.

11. The method of claim 1 wherein said membrane material carries bone marrow stromal cells.

12. The method of claim 1 further comprising implanting a resorbable bone mineral implant material into a region of bone injury in the area to be treated, prior to fixing said patch over said area to be treated.

13. The method of claim 12, wherein said bone mineral is charged with chondrocytes.

14. The method of claim 1, wherein said patch is charged with chondrocytes.

15. The method of claim 1 wherein said patch is comprised of a single barrier layer.

16. The method of claim 1 wherein said patch comprises said matrix layer sandwiched between one said barrier layer and a second said barrier layer.

17. The method of claim 1 wherein the matrix layer is provided by collagen II material derived from natural cartilage.

18. The method of claim 17 wherein the collagen II material is derived from hyaline cartilage from pigs.

19. The method of claim 17 wherein the collagen II material is physically cross linked.

20. The method of claim 1 wherein said at least one barrier layer is derived from peritoneum membrane from calves or pigs.

* * * * *